US010317260B2

(12) United States Patent
Duke et al.

(10) Patent No.: US 10,317,260 B2
(45) Date of Patent: Jun. 11, 2019

(54) YIELD DATA CALIBRATION METHODS

(71) Applicant: Farmers Edge Inc., Winnipeg (CA)

(72) Inventors: Guy Dion Duke, Lethbridge (CA);
Kevin John Grant, Lethbridge (CA)

(73) Assignee: Farmers Edge Inc., Winnipeg (CA)

( * ) Notice: Subject to any disclaimer, the term of this patent is extended or adjusted under 35 U.S.C. 154(b) by 238 days.

(21) Appl. No.: 15/134,358

(22) Filed: Apr. 20, 2016

(65) Prior Publication Data

US 2016/0313151 A1    Oct. 27, 2016

Related U.S. Application Data

(60) Provisional application No. 62/150,766, filed on Apr. 21, 2015.

(51) Int. Cl.
G01D 18/00      (2006.01)
G01N 33/24      (2006.01)
G06Q 10/06      (2012.01)
G06Q 50/02      (2012.01)

(52) U.S. Cl.
CPC ............ G01D 18/00 (2013.01); G01N 33/24 (2013.01); G06Q 10/06 (2013.01); G06Q 10/0639 (2013.01); G06Q 50/02 (2013.01); G01N 2033/245 (2013.01)

(58) Field of Classification Search
CPC ... G01D 18/00; G01N 33/24; G01N 2033/245
See application file for complete search history.

(56) References Cited

U.S. PATENT DOCUMENTS

| 5,764,819 | A | 6/1998 | Orr et al. |
| 5,995,894 | A | 11/1999 | Wendte |
| 6,236,907 | B1 | 5/2001 | Hauwiller et al. |
| 6,505,146 | B1 | 1/2003 | Blackmer |
| 7,047,133 | B1 | 5/2006 | Dyer et al. |
| 7,058,197 | B1 | 6/2006 | McGuire et al. |
| 8,731,836 | B2 | 5/2014 | Lindores et al. |
| 8,816,262 | B2 | 8/2014 | Holland |

(Continued)

FOREIGN PATENT DOCUMENTS

| RU | 2152147 C1 | 7/2000 |
| RU | 2007110484 A | 9/2008 |
| RU | 2008120611 A | 12/2009 |

OTHER PUBLICATIONS

PCT International Search Report and Written Opinion, PCT Application No. PCT/CA2016/050453, dated Jun. 6, 2016, 11 pages.

(Continued)

Primary Examiner — Ajay Ojha
(74) Attorney, Agent, or Firm — Goodhue, Coleman & Owens, P.C.

(57) ABSTRACT

Embodiments relate to calibrating yield data points. A calibration system receives a plurality of groups of yield data points. Each group is associated with an attribute, such as, a machine identifier, a zone identifier, a localized zone identifier, and/or a moisture identifier. The system calculates a grand aggregate yield based on the yield data points of the plurality of groups. The system calculates a group aggregate yield based on yield data points of each group. The system subtracts the group aggregate yield from each yield data point of the group producing adjusted yield data points. The system adds the grand aggregate yield to each of the adjusted yield data points producing calibrated yield data points.

21 Claims, 16 Drawing Sheets

(56) References Cited

U.S. PATENT DOCUMENTS

2012/0173185 A1 7/2012 Taylor et al.
2014/0358466 A1 12/2014 Foster et al.

OTHER PUBLICATIONS

"GIS Ag Maps—about p. c.: About Yield Monitor Calibration and Yield Map Post-Calibration," Agricultural and Mountain-related GIS and Remote Sensing Data and Information, 2011, 4 pages, [Online] [Downloaded Oct. 25, 2016] Retrieved from the Internet<URL:http://www.gisagmaps.com/about-post-calibration>.
USEPA, Statistical Analysis of Groundwater Monitoring Data at RCRA Facilities—Unified Guidance, US EPA, Mar. 2009, 888 pages.
Dean, R.B. et al., "Simplified Statistics for Small Numbers," Analytical Chemistry, Apr. 1951, pp. 636-638, vol. 23, No. 4.
Rosner, B., "Percentage Points for a Generalized ESD Many-Outlier Procedure," Technometrics, May 1983, pp. 165-172, vol. 25, No. 2.

YIELD DATA CALIBRATION METHODS

CROSS REFERENCE TO RELATED APPLICATIONS

This application claims the benefit of U.S. Provisional Application 62/150,766, filed on Apr. 21, 2015, which is incorporated by reference in its entirety.

BACKGROUND

1. Field of the Disclosure

This disclosure generally relates to data calibration, and more specifically to post-harvest yield data calibration.

2. Description of the Related Art

Modern GPS-based control systems in machines such as, for example, combine harvesters allow producers to collect crop information (e.g., yield information) at sampled points (e.g., yield data points) while a field is being harvested. The types of information collected differ depending on the make and model of the measuring instrument. Commonly collected information includes instantaneous yield information (e.g. bushels per acre (bu/ac)), location information, moisture levels, and machine and/or implement settings (e.g., rotations per minute, fuel consumption, etc.).

As with many measurement instruments, the accuracy of these measuring instruments vary for a number of reasons (e.g. global positioning system (GPS) drift, damage, temperature fluctuation, etc.). An important component in maintaining accuracy is calibration, which can be defined as the adjustment of a measuring instrument with a known standard. One specific example includes adjusting the levels of an on-board, or otherwise connected, moisture sensor to match a known result from a trusted source, such as, for example, the readings obtained from an external data source such as, for example, a ground based machine.

There is considerable value in a properly calibrated measuring instrument, however, calibration is a process that is not always performed, and calibration problems can intensify as machines progress through a field during a harvest.

SUMMARY

A system is provided that allows for calibrating yield data points. A calibration system receives a plurality of groups of yield data points. Each group is associated with an attribute, such as, a machine identifier, a zone identifier, a localized zone identifier, and/or a moisture identifier. The system calculates a grand aggregate yield based on the yield data points of the plurality of groups. The system calculates a group aggregate yield based on yield data points of each group. The system subtracts the group aggregate yield from each yield data point of the group producing adjusted yield data points. The system adds the grand aggregate yield to each of the adjusted yield data points producing calibrated yield data points.

In some configurations, the grand aggregate yield is a grand mean yield and the group aggregate yield is a group mean yield. In other configurations, the grand aggregate yield is a grand median yield and the group aggregate yield is a group median yield.

In some configurations, the system determines a set of yield data points including yield data points within a threshold distance of each yield data point and calibrates the yield data point based on the set of yield data points producing a neighbor-calibrated yield data point.

In some configurations, the system receives a confidence parameter associated with the attribute for each group and calibrates the yield data points of the group based on the confidence parameter.

In some configurations, the system accesses a predetermined adjustment value associated with the attribute for each group and adjusts each of the calibrated yield data points by the predetermined adjustment value. The adjustment value can be a number or a percentage.

BRIEF DESCRIPTION OF THE DRAWINGS

The teachings of the embodiments described herein can be readily understood by considering the following detailed description in conjunction with the accompanying drawings.

Reference will now be made in detail to several embodiments, examples of which are illustrated in the accompanying figures. It is noted that wherever practicable similar or like reference numbers may be used in the figures and may indicate similar or like functionality. The figures depict embodiments of the described system (or method) for purposes of illustration only. One skilled in the art will readily recognize from the following description that alternative embodiments of the structures and methods illustrated herein may be employed without departing from the principles described herein.

DETAILED DESCRIPTION

Collecting crop information allows producers to produce detailed analysis of production costs and returns, enabling strategic planning in future crop iterations. For example, variability in yield data points can be an indication of management zone boundaries, which can be used to develop custom prescriptions for variable-rate fertilizer operations. Computing aggregate yield information (e.g., bu/ac), as both an absolute measure (e.g., determining the number of bushels that a field produced) and as a relative measure (e.g., comparing production rates between two management zones) involves computing a continuous value from a set of discrete samples (and thus requires further information, such as speed and direction of a machine at the instance of yield data collection).

With increases in farm sizes, coupled with the advent of large custom harvesting operations, the net result is that fields are often cut by more than one machine. If two machines are not calibrated correctly, then the machines can produce different results under the same conditions (i.e. a problem of precision in addition to accuracy). Imprecision between machines can produce inaccurate comparisons within a field. As an example, a machine whose yield monitor is biased in a positive direction will estimate higher yields than a machine whose yield monitor is not bias (or is biased in a negative direction). As a result, when computing field-based or zone-based return-on-investment (ROI) estimates, differences may be reported that are a result of poor calibration, rather than a result of true variation amongst the yields.

Figure 3:
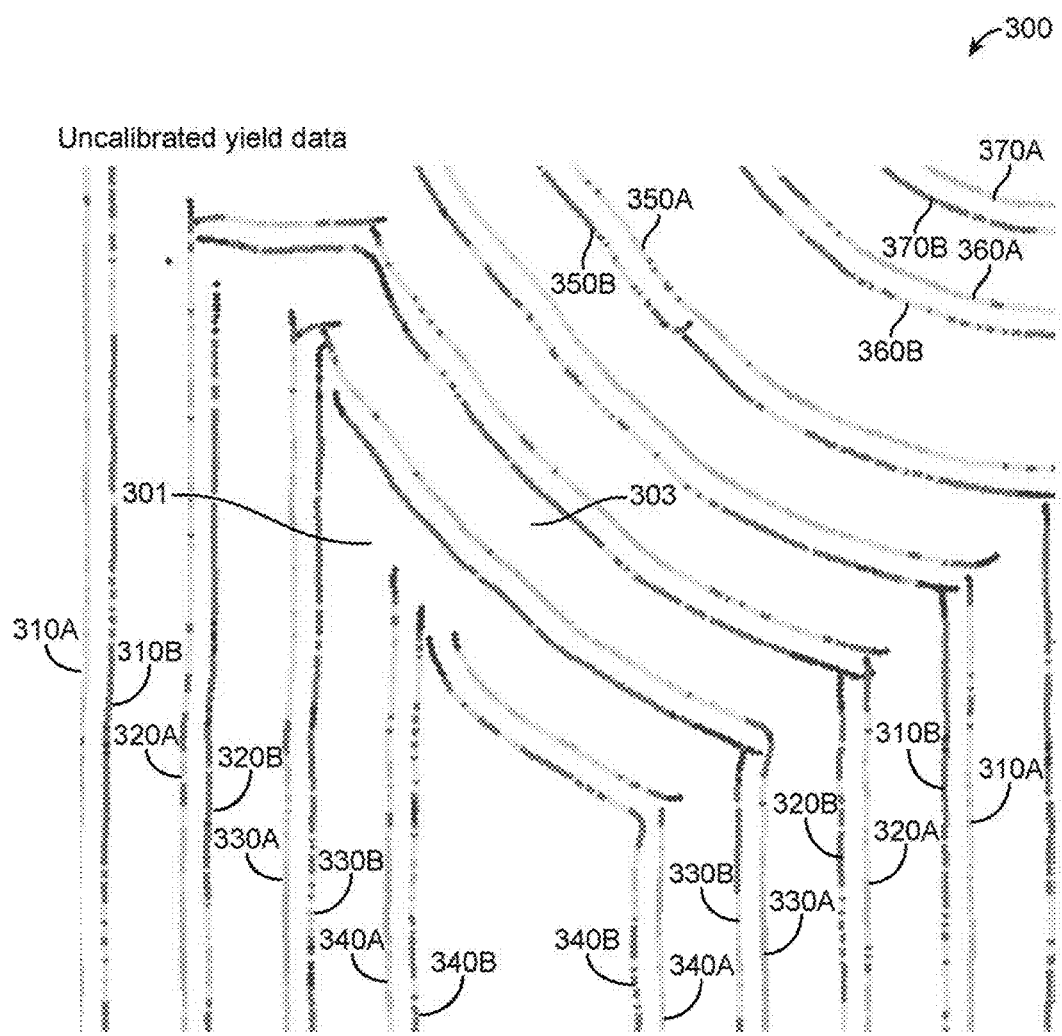
FIG. 3 illustrates uncalibrated yield data points, according to one embodiment.

Referring briefly to figure (FIG. 3, FIG. 3 illustrates uncalibrated yield data points collected from two machines over a field 300 under similar conditions. 310A, 320A, 330A, 340A, 350A, 360A, and 370A illustrate uncalibrated yield data lines captured by a first machine (e.g. machine 102 and/or implement 104 coupled to the machine 102) and 310B, 320B, 330B, 340B, 350B, 360B, and 370B illustrate uncalibrated yield data lines captured by a second machine (e.g. machine 102 and/or implement 104 coupled to the machine 102). Each yield data line includes a plurality of yield data points. FIG. 3 illustrates a particularly striking case of machine variability. 301 identifies at a light gray line, representing 38-45 bu/ac collected by the first machine, and 303 identifies at a dark gray line, representing 22-31 bu/ac collected by the second machine. Towards the left edge of the field 300, the yield data lines collected from the first and second machines alternate in productivity, suggesting a high correlation between machine and yield data points. Across the field 300, the two machines produced averages that differed considerably: a mean of 38.38 for the yield data points collected by the first machine and a mean of 30.71 for yield data points collected by the second machine. A simple t-test highly suggests that the two sets of yield data points are not from the same distribution (T=−6.2596, p<10e-10). Visually, under perfect calibration, any two corresponding yield data lines (yield data points collected from different machines) running through the same management zone under similar conditions should be a similar color.

Calibrating the yield data points captured by the first and second machines can resolve machine variability issues. Calibration can include calculating statistics of the yield data points captured by the first and second machines, and adjusting the yield data points captured by the first and second machines based on the calculated statistics.

I. Configuration Overview

Figure 1:
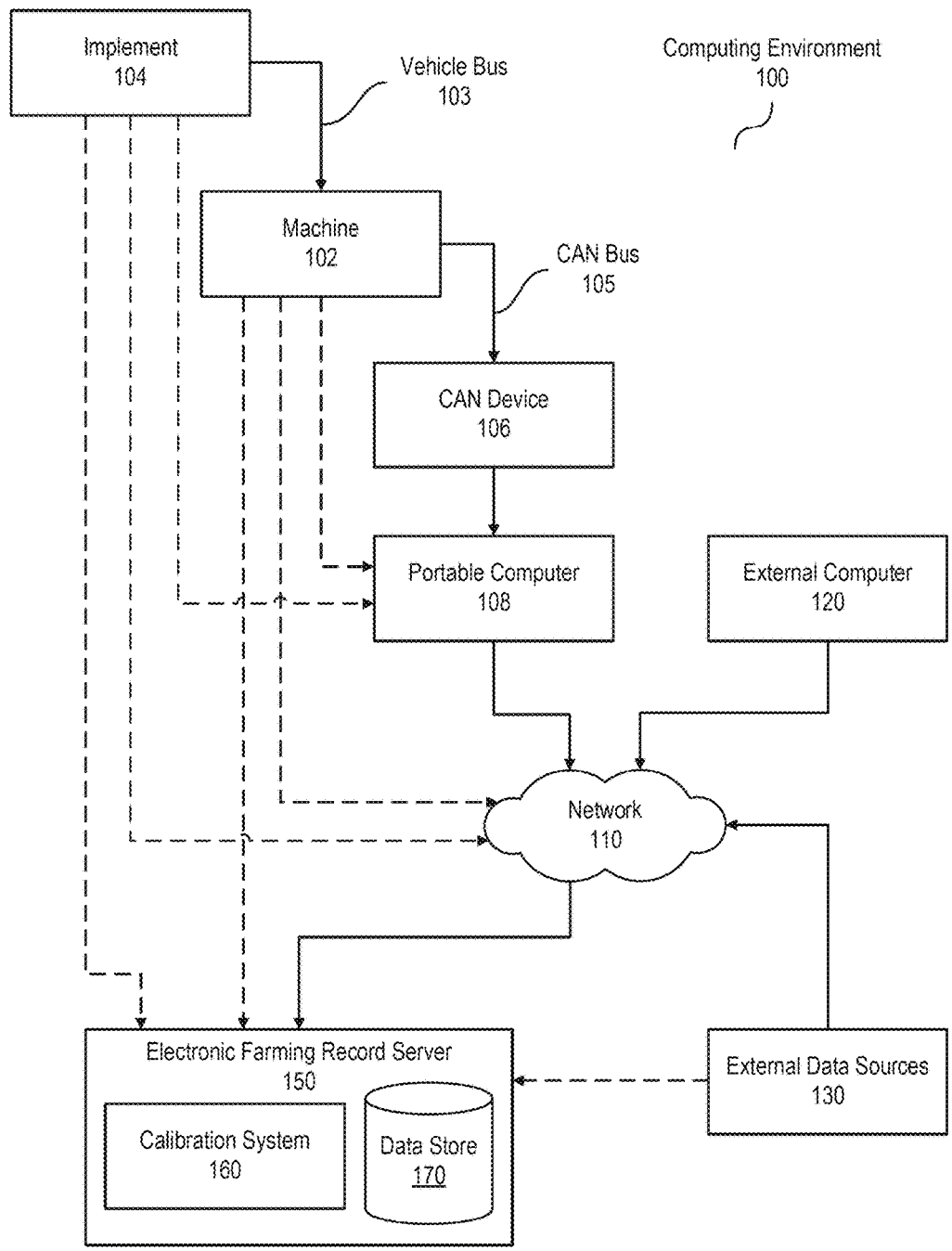
FIG. 1 illustrates a block diagram of a computing environment including agricultural equipment moving through a field, according to one embodiment.

FIG. 1 illustrates a block diagram of a computing environment including agricultural equipment moving through a field, according to one embodiment. The computing environment 100 includes a machine 102, an implement 104, a controller area network (CAN) device 106, a portable computer 108, an external computer 120, external data sources 130, and an electronic farming record server 150. The portable computer 108, the external computer 120, the external data sources 130, and the electronic farming record server 150 include computing devices that may be physically remote from each other but which are communicatively coupled by the network 110. The network 110 is typically the Internet, but can be any network(s), including but not limited to a LAN, a MAN, a WAN, a mobile wired or wireless network, a private network, a virtual private network, or a combination thereof.

The machine 102 enables a user (e.g., farmer and/or farming business) to plant, harvest, treat, and otherwise manage crops. The machine 102 captures, stores, and shares farming operation data generated by the machine 102 and/or the implement 104. Examples of farming operation data include crop type and variety information, seeding information, chemical application information (e.g., fertilizer application information, pesticide application information, etc.), soil chemical properties, fuel usage information of the machine 102 and/or the implement 104, weather information, terrain elevation information, and imagery (e.g., satellite imagery, aircraft imagery, etc.). Farming operation data is compiled according to field characteristics, such as, for example, yield data points. Yield data points include instantaneous yield information (e.g., bushels per acre (bu/ac)).

The remainder of this description discusses yield data points specifically, however in practice the calibration techniques and any other operations described herein may also be performed on any other kind of farming operation data collected by the machine 102 or the implement 104, and are equally applicable to them as well.

The machine 102 (or implement 104, device 106, computer 108, or server 150) modifies the yield data points to include one or more attributes, such as, for example, information regarding a machine identifier identifying the machine 102 and a moisture identifier identifying moisture content associated with the yield data points. The information regarding the machine identifier, the zone identifier, the localized zone identifier, and the moisture identifier can be included in metadata of the yield data points. The machine 102 includes computer systems and controllers. Examples of machines 102 include tractors, planters, and combine harvesters, as well as machines not necessarily associated with farming such as flying, remote-operated drones.

The machine 102 is coupled to the implement 104 via a vehicle bus 103. Although FIG. 1 illustrates the machine 102 as being coupled to one implement 104, in practice, the machine 102 can be coupled to more than one implement 104. The vehicle bus 103 can operate according to Society of Automotive Engineers (SAE) J1939. SAE J1939 is used for communication and diagnostics among the implement 104 and the machine 102. The vehicle bus 103 may be, more specifically, a CAN bus. The CAN bus may operate according to International Organization for Standardization (ISO) 11783 known as "Tractors and machinery for agriculture and forestry—Serial control and communications data network." ISO 11783 is a communication protocol commonly used in the agriculture industry and is based on SAE J1939. However, in other embodiments the vehicle bus 103 may use an alternative data exchange mechanism, such as Ethernet wiring and a network transmission protocol such as TCP/IP.

The implement 104 is any agricultural machinery used on a farm to aid and/or assist in farming. The implements 104 can be used in soil cultivation, planting, fertilizing, controlling pests, irrigation, harvesting/post-harvesting, and/or sorting yield. The implement 104 captures the yield data points and transmits the captured yield data points to the machine 102 via the vehicle bus 103.

The machine 102 is communicatively coupled to the CAN device 106 via a CAN bus 105. The CAN device 106 is configured to interpret vehicle bus 103 messages and convert them for interpretation by a portable computer 108 and the electronic farming record server 150 for use in the calibration system 160. The CAN device 106 is further communicatively coupled to the portable computer 108. The CAN device 106 receives the modified yield data points from the machine 102 via the CAN bus 105, processes the received modified yield data points, and transmits the processed yield data points to the portable computer 108.

In some configurations, either the implement 104 or machine 102 collecting the data or the CAN device 106 may be communicatively coupled directly to the portable computer 108, or server 150 through network 110. In these configurations, these components transmits the processed yield data points more directly to the electronic farming record server 150 without the need for intermediate devices such as the CAN device 106 or the portable computer 108. For example, either an implement 104 or a machine 102 may include a wireless communication device allowing communications through network 110.

In other configurations, either the implement 104, the machine 102, or the external data sources 130 collecting or otherwise providing the data may be communicatively coupled directly the server 150. In these configurations, these components transmit yield data points and/or information captured by data sources external to the implement 104 and/or the machine 102 more directly to the electronic farming record server 150 without the need for the intermediate network 110. For example, an implement 104, a machine 102, or an external data source 130 may include a wired communication interface (e.g., a Universal Serial Bus (USB) interface) allowing communication to the electronic farming record server 150.

The portable computer 108 allows the user (e.g., the farmer and/or the farming business) to interface with the processed yield data points received from the CAN device 106. The portable computer 108 and an external computer 120 allow users to access and interact with data stored on the server 150. Examples of a portable computer 108 and an external computer 120 include a personal computer, a laptop, a personal digital assistant, or a cellular, mobile, or smart phone.

The external data sources 130 provide information captured by data sources external to the machine 102 and/or the implement 104. Examples of external data sources 130 include weather stations, geographical information systems (GIS), image databases (e.g., satellite image databases, aircraft image databases, etc.), and the like. These data sources may include spatially varying data (such as spatially varying satellite images of the fields in which a machine 102 is travelling), and thus can provide granular data that is at a same or similar spatial resolution to the yield data points gathered by the machine 102.

The electronic farming record server 150 processes the yield data points received from the portable computer 108 together with information received from the external data sources 130. For example, the electronic farming record server 150 processes the yield data points received from the portable computer 108 to include one or more attributes, such as, a zone identifier identifying a zone in the field and a localized zone identifier identifying a localized zone in the field. The electronic farming record server 150 includes a calibration system 160. The calibration system 160 calibrates the yield data points.

Figure 2:
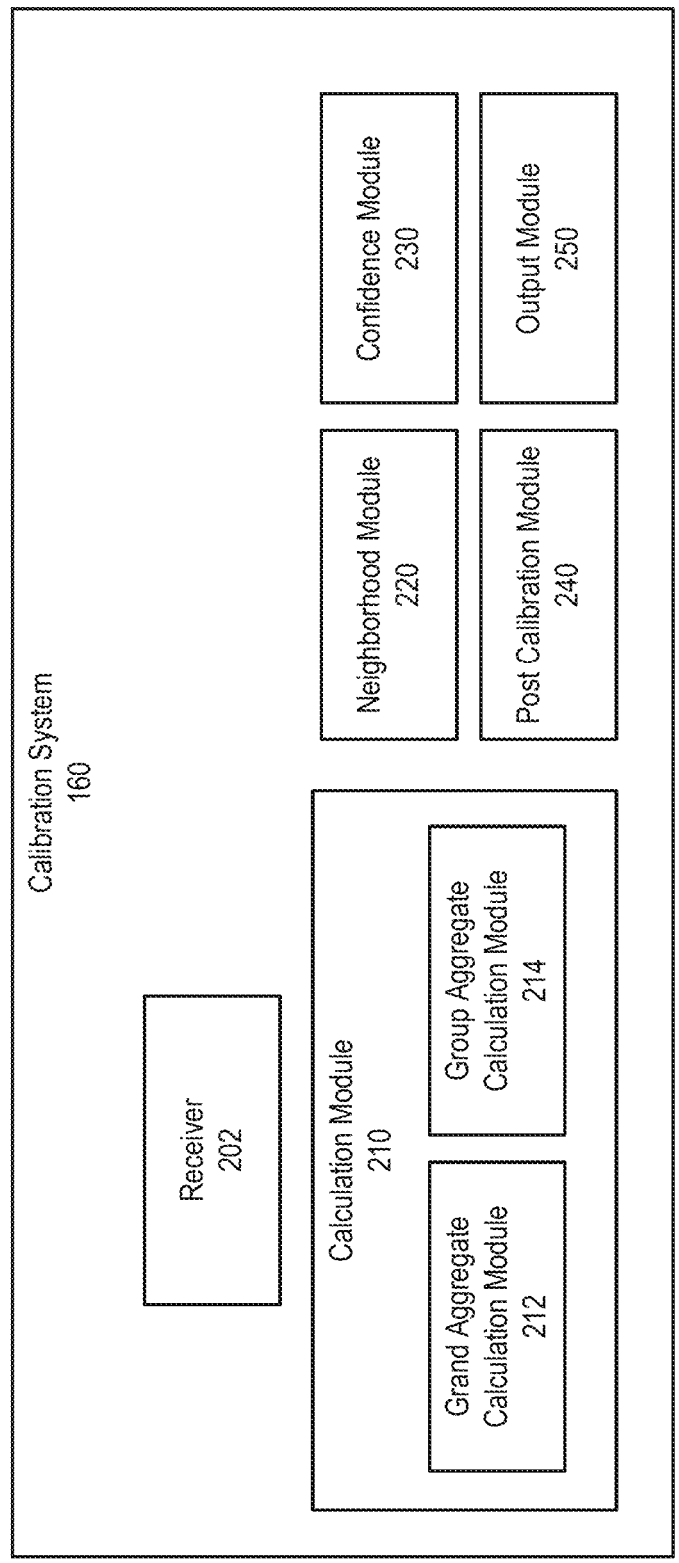
FIG. 2 illustrates a block diagram of the logical components of a calibration computer system for calibrating yield data points, according to one embodiment.

FIG. 2 illustrates the calibration system 160, according to one embodiment. The calibration system 160 includes a receiver 202, a calculation module 210, a neighborhood module 220, a confidence module 230, a post calibration module 240, and an output module 250. The receiver 202 receives a plurality of groups of yield data points and any other data used to perform calibration of the data, including data from the external data sources 130. The output module 250 outputs calibrated yield data points. Generally, the receiver 202 will pass the yield data points to one or more other modules from FIG. 2, which will in turn provide their output to the output module 250 for storage in a data store 170 and for presentation to the user. Further, these individual modules may pass data to each other as needed to perform calibration or depending upon how the various modules are combined and ordered to perform a complete calibration. The exact calibrations performed in any given implementation may vary, and thus the ordering and passing of data between modules may also vary by implementation.

The calculation module 210 calculates aggregate yields based on the yield data points received from the receiver 202. The calculation module 210 includes a grand aggregate calculation module 212 and a group aggregate calculation module 214. The grand aggregate calculation module 212 calculates a grand aggregate yield based on the yield data points of the plurality of groups. In some configurations, the grand aggregate yield is a grand mean yield and, in other configurations, the grand aggregate yield is a grand median yield. The group aggregate calculation module 214 calculates group aggregate yield based on yield data points of a group. The breakdown of what constitutes a group will be further described in the following sections with respect to each individual type of calibration. In some configurations, the group aggregate yield is a group mean yield and, in other configurations, the group aggregate yield is a group median yield.

The neighborhood module 220 determines a set of yield data points including yield data points within a threshold proximity of a yield data point. The neighborhood module 220 calibrates the yield data points based on the set of yield data points, thereby producing a neighbor-calibrated yield data point.

The confidence module 230 receives a confidence parameter along with the attributes associated with the yield data points and calibrates yield data points of a group based on the received confidence parameter. The post calibration module 240 accesses a predetermined adjustment value for a group where the predetermined adjustment value is associated with the attribute. The post calibration module 240 adjusts each of the calibrated yield data points by the predetermined adjustment value. The predetermined adjustment value is a number, a percentage, or combination thereof.

II. Initial Calibration

Figure 4:
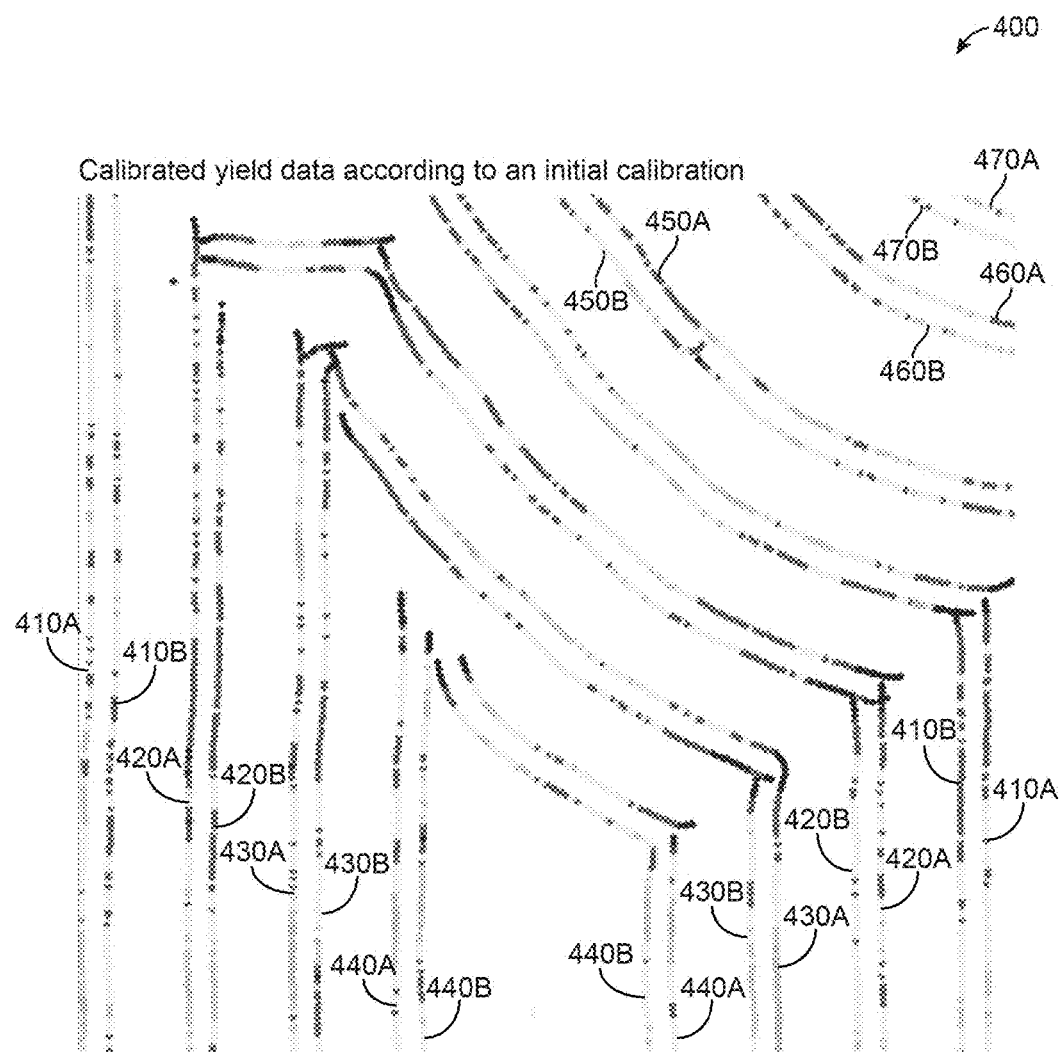
FIG. 4 illustrates yield data points of FIG. 3 calibrated according to an initial calibration method, according to one embodiment.

An initial calibration method is outlined as follows:

1) Receive, by the receiver 202, groups of yield data points on a per field basis, each group associated with an attribute, such as, for example, a machine identifier;

2) Calculate, by the grand aggregate calculation module 212, a grand (overall) mean yield volume based on the yield data points of the groups;

3) Group, by the calculation module 210, the yield data points according to machine identifier;

4) For each group (e.g., machine, implement):

a) Calculate, by the group aggregate calculation module 214, a group mean yield volume based on the yield data points of the group;

Table 1 shows a set of key statistics for the uncalibrated and calibrated datasets as illustrated in FIG. 3 and FIG. 4, respectively. The uncalibrated and calibrated datasets each include statistics regarding grand (overall) of both first and second machines, a first machine, and a second machine. The statistics of the calibrated dataset is determined from yield data points calibrated according to the initial calibration. The grand mean and grand median values of the uncalibrated and calibrated datasets are nearly equivalent, while the standard deviation of the calibrated dataset is significantly lower than that of the uncalibrated dataset. As the two distributions from the two machines are brought closer together, the spread between the non-overlapping tails of each distribution is reduced. In other words, as uncalibrated yield data points are calibrated, the standard deviation of the yield data points is lowered. The mean and median of the first machine of the uncalibrated dataset are significantly higher than the mean and median of the first machine of the calibrated dataset. Similarly, the mean and median of the second machine of the uncalibrated yield dataset are significantly lower than the mean and median of the second machine of the calibrated dataset.

TABLE 1

| Uncalibrated | | Calibrated | |
| --- | --- | --- | --- |
| Grand (Overall) | | Grand (Overall) | |
| Mean | 34.6233489225 | Mean | 34.6233489225 |
| Standard Deviation | 8.48941772178 | Standard Deviation | 7.57486912857 |
| Median | 34.52455 | Median | 34.7776771098 |
| First Machine | | First Machine | |
| Mean | 38.3817204334 | Mean | 34.6233489225 |
| Standard Deviation | 7.74454078124 | Standard Deviation | 7.74454078124 |
| Median | 38.4938 | Median | 34.7354284891 |
| Second Machine | | Second Machine | |
| Mean | 30.714323192 | Mean | 34.6233489225 |
| Standard Deviation | 7.39426676994 | Standard Deviation | 7.39426676994 |
| Median | 30.9063 | Median | 34.8153257305 | b) Subtract, by the calculation module 210, the group mean yield volume for each yield data point of the group producing adjusted yield data points;

c) Add, by the calculation module 210, the grand mean yield volume to each of the adjusted yield data points producing calibrated yield data points.

FIG. 3 illustrates uncalibrated yield data points from two machines over a field 300 and FIG. 4 illustrates calibrated yield data points via an initial calibration method over a field 400. Referring to FIG. 4, 410A, 420A, 430A, 440A, 450A, 460A, and 470A illustrate calibrated yield data lines captured by the first machine and calibrated according to the initial calibration method, and 410B, 420B, 430B, 440B, 460B, and 470B illustrate calibrated yield data lines captured by the second machine and calibrated according to the initial calibration method. Each yield data line includes a plurality of yield data points. Yield data lines running beside each other (yield data lines from the first machine and yield data lines from the second machine) show better equivalence (similar shades of gray), which is an improvement even though no spatial considerations are made during the initial calibration method. The yield data lines also show much less correlation with machine (i.e., is less cyclical rising and lowering of values).

A one-way analysis of variance (ANOVA) test shows a significant statistical difference between the two machines' data before calibration ($F=5565.03$, $p<0.0001$), whereas no statistical difference following calibration ($F<10e-8$, $p>0.9999$).

III. Outliers

Outliers can severely impact the results of any data analysis. Outliers can occur in yield data points due to many factors such as machine start- and end-pass delay, machine/implement malfunction, machine turning, etc. One way to mitigate the effect of outliers is to use the median instead of the mean in the calculations outlined in the initial calibration method. Medians are useful in the place of a mean when data is not normally distributed. Medians are less sensitive to statistical outliers than means are, particularly for smaller datasets.

An outlier method is outlined as follows:

1) Receive, by the receiver 202, groups of yield data points on a per field basis, each group associated with an attribute, such as, for example, a machine identifier;

2) Calculate, by the grand aggregate calculation module 212, a grand (overall) median yield volume based on the yield data points of the groups;

3) Group, by the calculation module 210, the yield data points according to machine identifier;

4) For each group (e.g., machine, implement):

a) Calculate, by the group aggregate calculation module 214, a group median yield volume based on the yield data points of the group;

b) Subtract, by the calculation module 210, the group median yield volume for each yield data point of the group producing adjusted yield data points;

c) Add, by the calculation module 210, the grand median yield volume to each of the adjusted yield data points producing calibrated yield data points.

Figure 5:
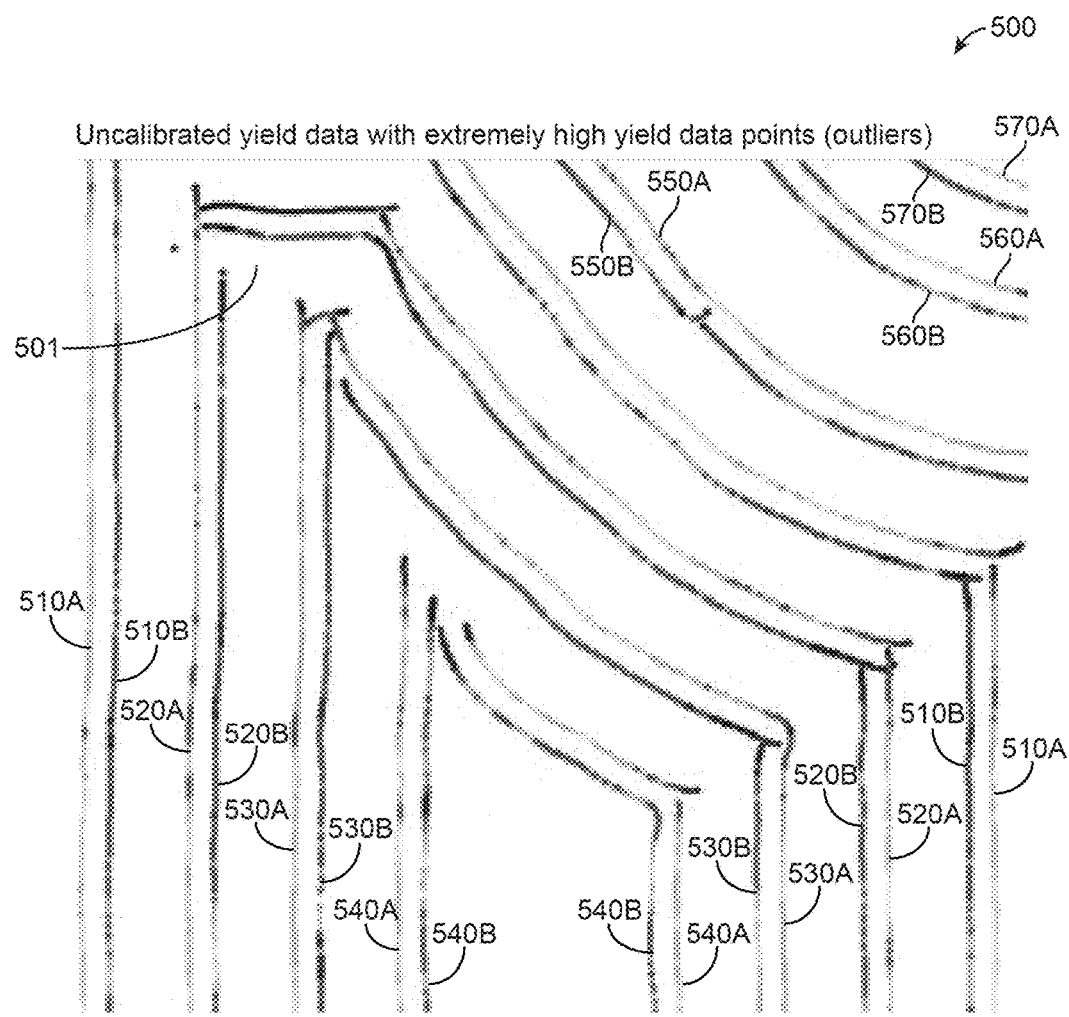
FIG. 5 illustrates uncalibrated yield data points with extremely high yield data point values added, according to one embodiment.
Figure 6:
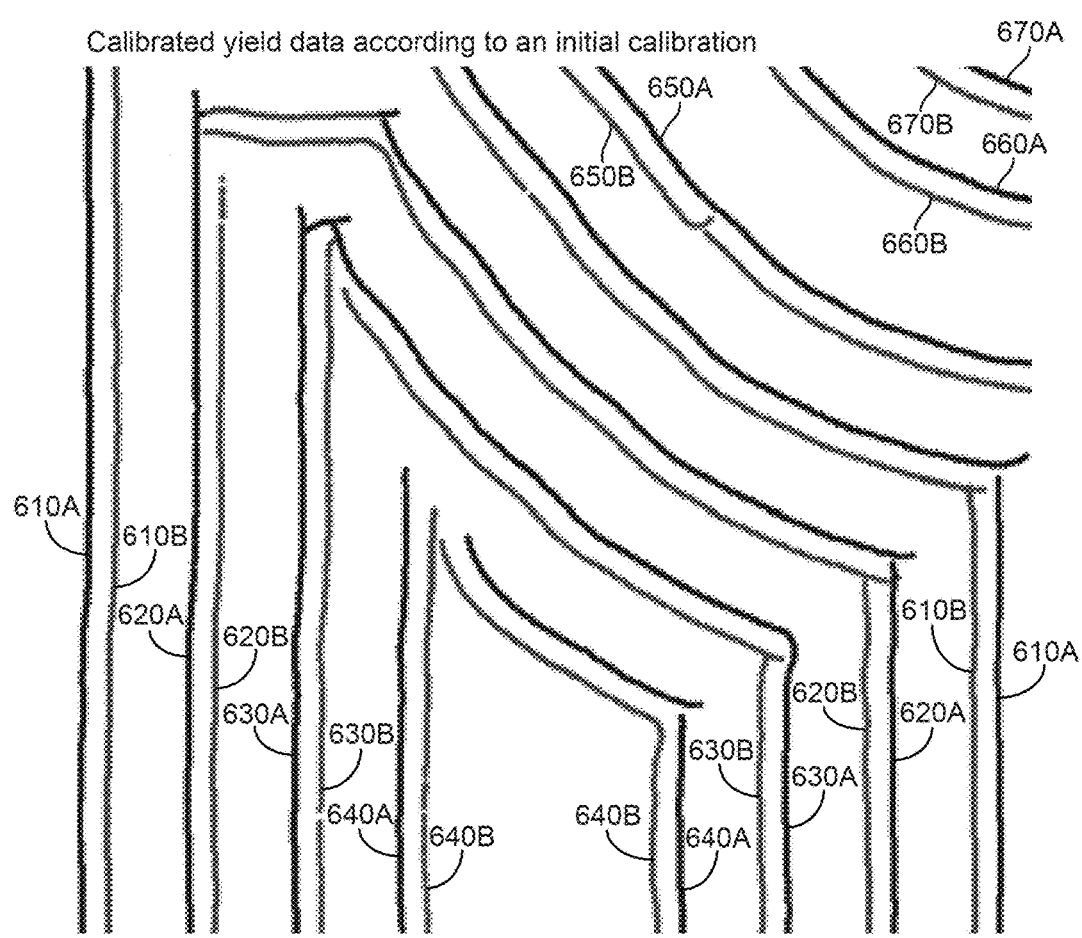
FIG. 6 illustrates yield data points of FIG. 5 calibrated according to an initial calibration method, according to one embodiment.
Figure 7:
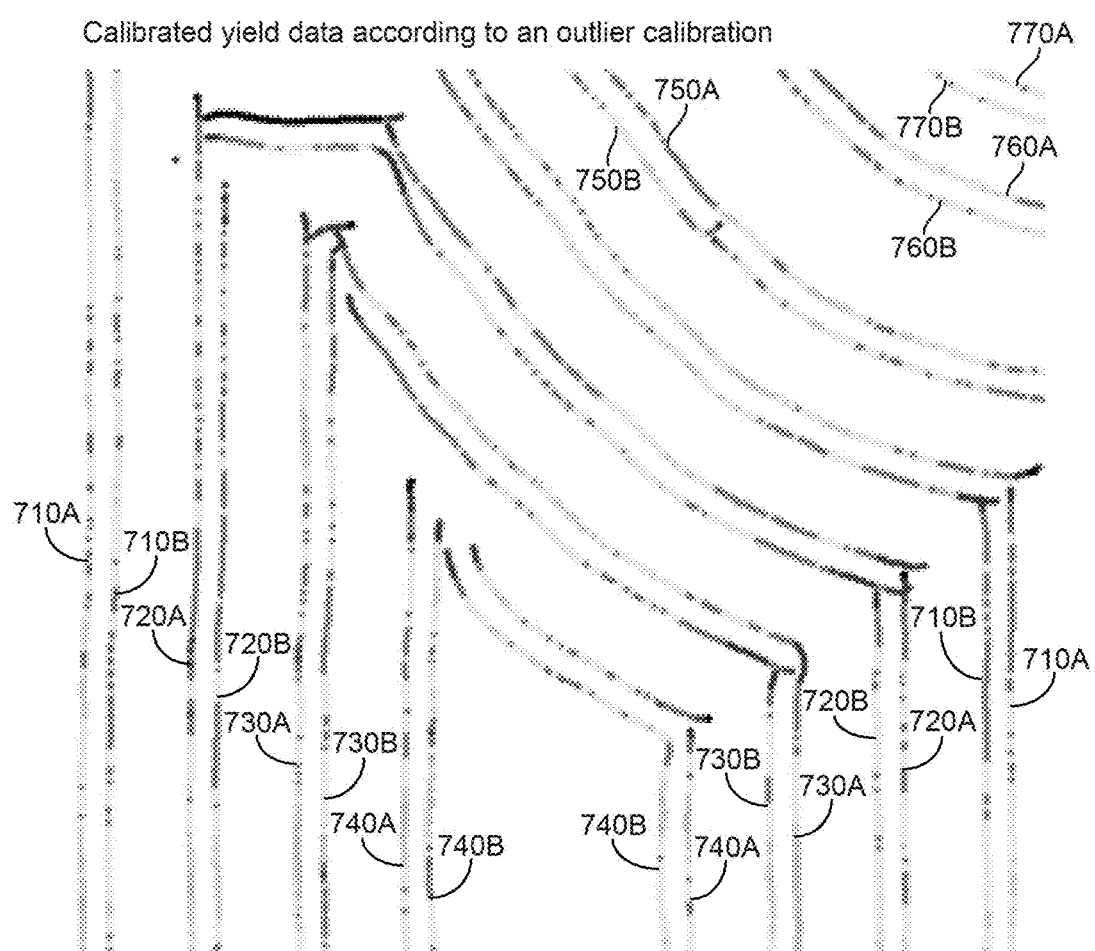
FIG. 7 illustrates yield data points of FIG. 5 calibrated according to an outliers method, according to one embodiment.

Consider FIG. 5 which illustrates un-calibrated yield data collected by two machines over a field 500. FIG. 5 illustrates a similar dataset as illustrated in FIG. 3, with some extremely large yield data points (yield data line 520A) added to the yield data points captured by the first machine, simulating outliers (the extreme dark gray line in the top left) indicated by 501. 510A, 520A, 530A, 540A, 550A, 560A, and 570A illustrate uncalibrated yield data lines captured by the first machine and 510B, 520B, 530B, 540B, 560B, and 570B illustrate uncalibrated yield data lines captured by a second machine. Each yield data line includes a plurality of yield data points. FIG. 6 illustrates calibrated yield data points via the initial calibration method, while FIG. 7 illustrates calibrated yield data points via the outlier method. Referring to FIG. 6, 610A, 620A, 630A, 640A, 650A, 660A, and 670A illustrate calibrated yield data lines captured by the first machine and calibrated according to the initial calibration method, and 610B, 620B, 630B, 640B, 660B, and 670B illustrate calibrated yield data lines captured by the second machine and calibrated according to the initial calibration method. Referring to FIG. 7, 710A, 720A, 730A, 740A, 750A, 760A, and 770A illustrate calibrated yield data lines captured by the first machine and calibrated according to the outlier method, and 710B, 720B, 730B, 740B, 760B, and 770B illustrate calibrated yield data lines captured by the second machine and calibrated according to the outlier method.

As illustrated in FIG. 6, the outliers can create an exaggerated global mean (which greatly inflates the yield data points from the second machine), as well as an exaggerated local mean (which greatly deflates the yield data points from the first machine). The yield data points in FIG. 6 illustrate the antithesis of what is desired: lines running beside each other are never the same color. The calibration outlined in the outlier method may be more appropriate in situations where the data is suspected to include outliers as illustrated in FIGS. 5-7.

IV. Data Partitioning

Figure 8B:
FIG. 8B illustrates moisture content at the yield data points of FIG. 8A, according to one embodiment.
Figure 8A:
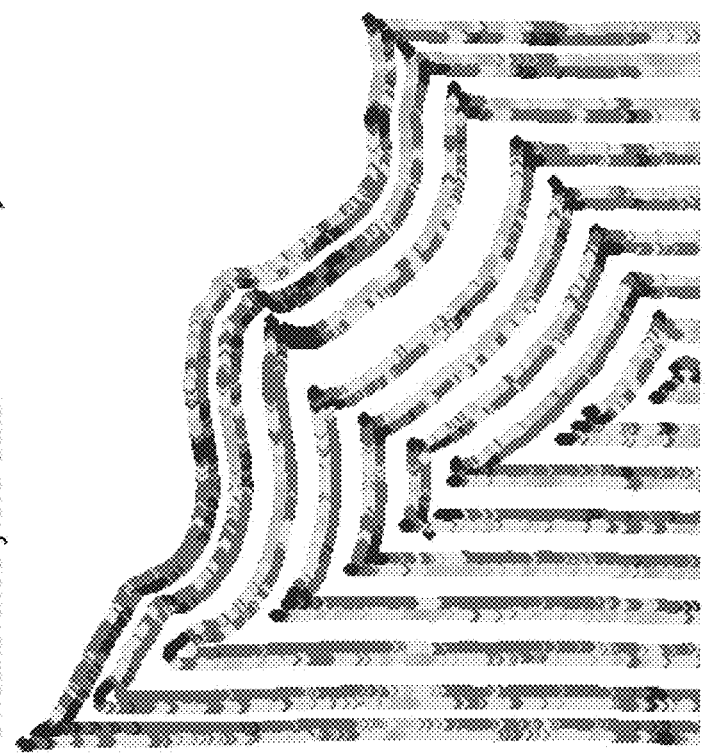
FIG. 8A illustrates uncalibrated yield data points, according to one embodiment.

One assumption made in the initial calibration and the outlier methods is that the distribution of yield data points between multiple machines are identical (assuming the machines service the same area under similar conditions); however, this is not always the case, as yield may vary significantly due to other factors, such as management zones. In one example, fertility between management zones differ and can produce true variation that should not be averaged away if two machines differ in their management zone coverage. Continuing the example, a user (e.g., a farmer and/or farming business) can purposely vary fertilizer rates in different areas of a field (e.g. control strips). In this example, the expected yield data variation should not be attributed to calibration issues, particularly in the case of correlation between these variations and machine coverage (e.g. a single machine cuts the control strip, while other machines cut the areas beside the control strip). Another example is date: if two machines operate over the same zone over different time periods, with only partial overlap, then variation in yield data due to harvest date should not be calibrated away. In one example, machines that operate in wetter areas are sometimes likely to report higher yield data point values. FIG. 8A illustrates uncalibrated yield data collected by two machines over a field 800 and FIG. 8B illustrates moisture content of the field 800 of FIG. 8A. In one example, the moisture content illustrated in FIG. 8B can be collected by the two machines that collected the yield data over the field 800 of FIG. 8A. In another example embodiment, the moisture content can be provided by an external data source (e.g., the external data source 130). As illustrated in FIG. 8B, the moisture levels vary considerably throughout the field 800, and that the wetter areas tend to correspond to higher uncalibrated yield data point values, as illustrated in FIG. 8A.

FIG. 8A illustrates that other variables besides yield data point calibration are at play, and these could affect the analysis if they are not controlled. One way to control for the effects of a variable is to hold the variable constant during calibration. From the management zone example, all yield data points in a first zone would be calibrated separately from all data points in a second zone, and so on. One method includes discretizing the yield data points and calibrating separately for each resulting yield data point. In other words, partitioning the yield data points into multiple groups, and computing/calibrating over each group separately.

Figure 9B:
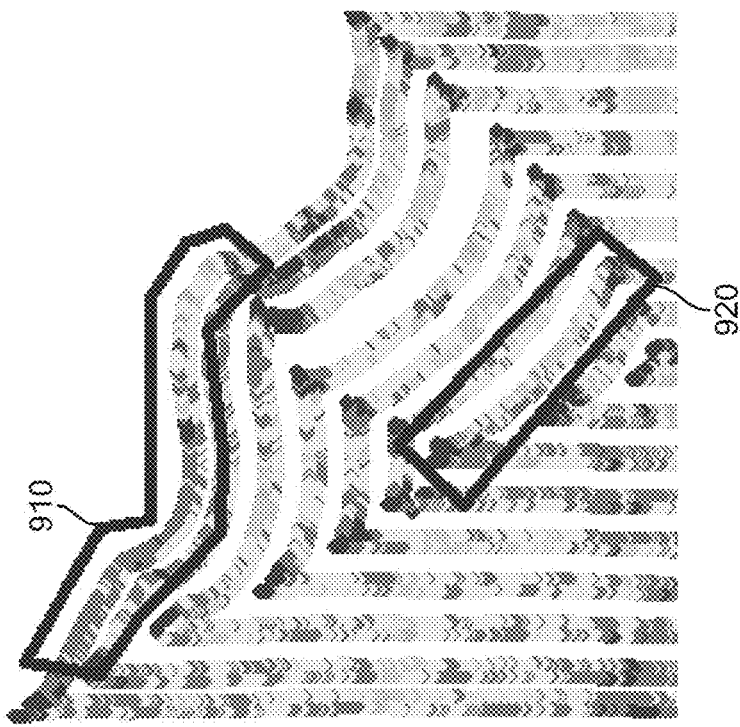
FIG. 9B illustrates yield data points of FIG. 8A calibrated according to partitioned calibration, according to one embodiment.
Figure 9A:
FIG. 9A illustrates yield data points of FIG. 8A calibrated according to un-partitioned calibration, according to one embodiment.

Attributes, such as, for example, zone identifiers, list of attributes, such as, for example, zone identifiers concatenated with discrete moisture levels, and function of attribute values, such as, for example, a custom discretization function for moisture levels, can be specified by the user. These attributes are held constant for each calibration operation. FIG. 9A illustrates the result of un-partitioned calibration. FIG. 9B illustrates the result of calibration after partitioning the data into 6 moisture zones according to moisture content data illustrated in FIG. 8B.

Because each machine had reasonably consistent coverage in each zone, the effects of this change are subtle. However, a few places of note have been highlighted (in dark gray) in FIG. 9B. The un-partitioned calibration, as illustrated in FIG. 9A, pushes the yield data point values of the two machines closer together, even though the detected moisture content, as illustrated in FIG. 8B, recorded by the two machines are noticeably different (likely owing to headland proximity). By contrast, the partitioned version, as illustrated in FIG. 9B, calibrates the different moisture zones separately, and the result is that the outside round 910 calibrates to a lower yield than the inside round 920.

A data partitioning method is outlined as follows:

1) Receive, by the receiver 202, groups of yield data points on a per field basis, each group associated with one or more attributes, such as, for example, a machine identifier, zone identifier, localized zone identifier, and moisture identifier;

2) Receive, by the receiver 202, attribute(s) and/or function(s) of attributes to hold constant;

3) Partition, by the calculation module 210, the yield data points into groups according to the received attribute(s);

4) Perform the initial calibration and/or outlier methods using the partitioned yield data points.

V. Grid-Based Calibration

Figure 10:
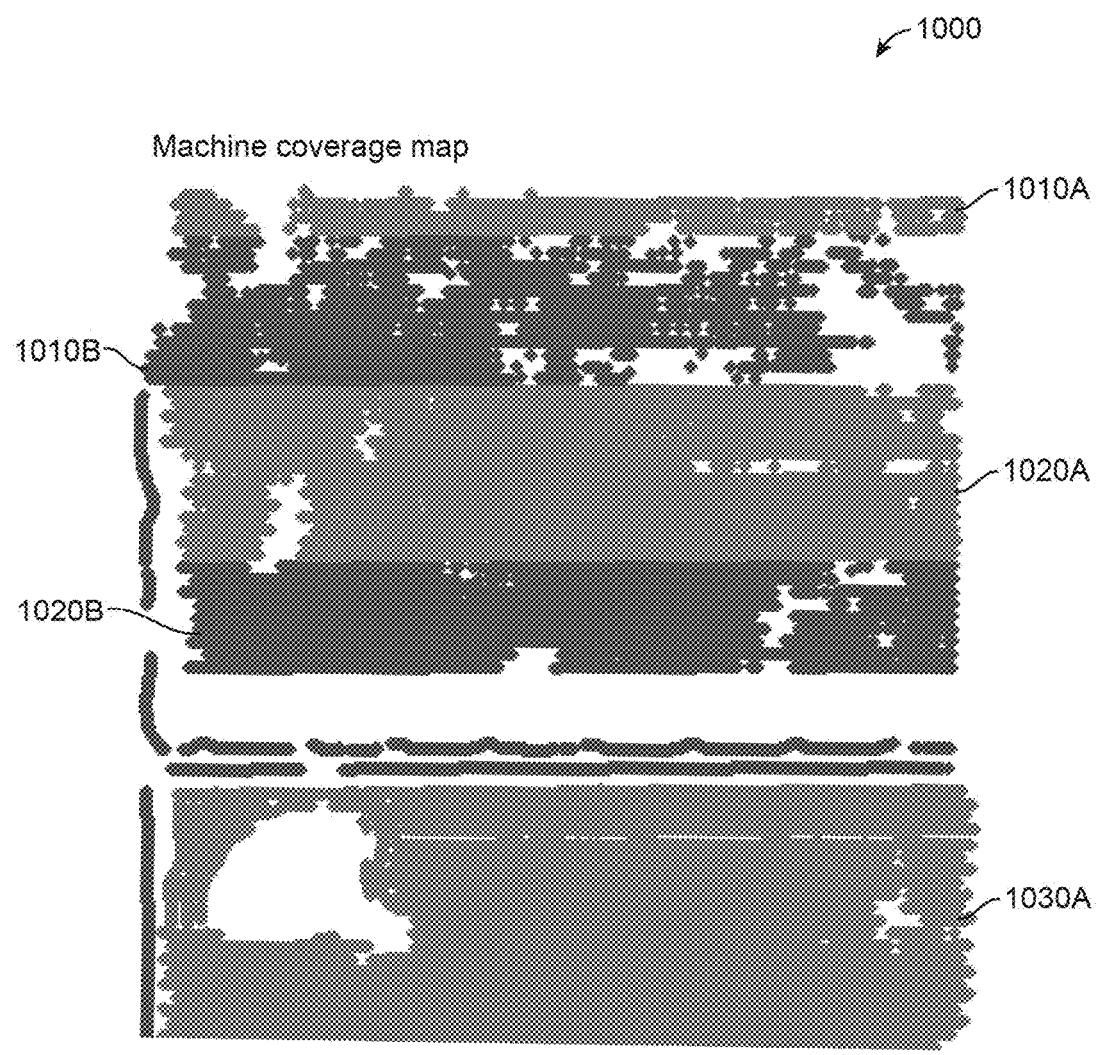
FIG. 10 illustrates a machine coverage map, according to one embodiment.
Figure 11B:
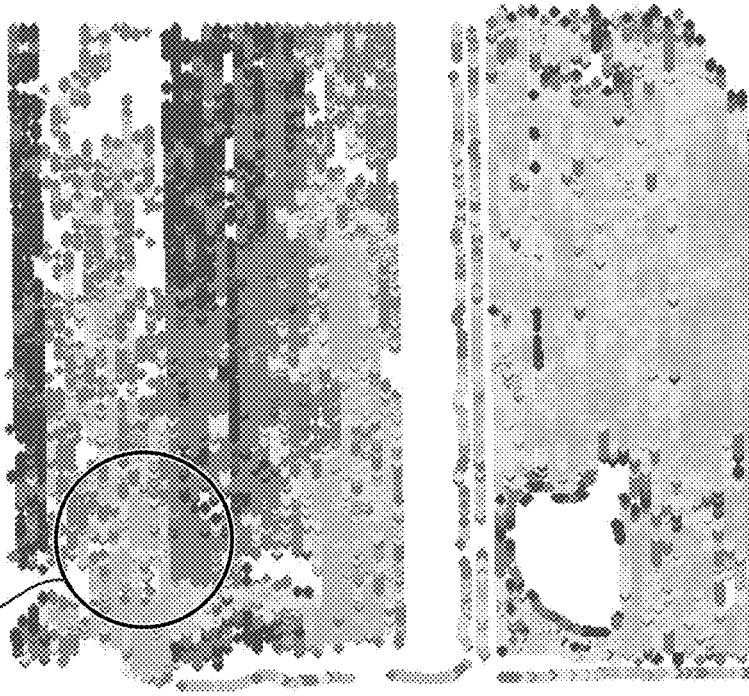
FIG. 11B illustrates calibrated yield data points of FIG. 11A, according to one embodiment.
Figure 11A:
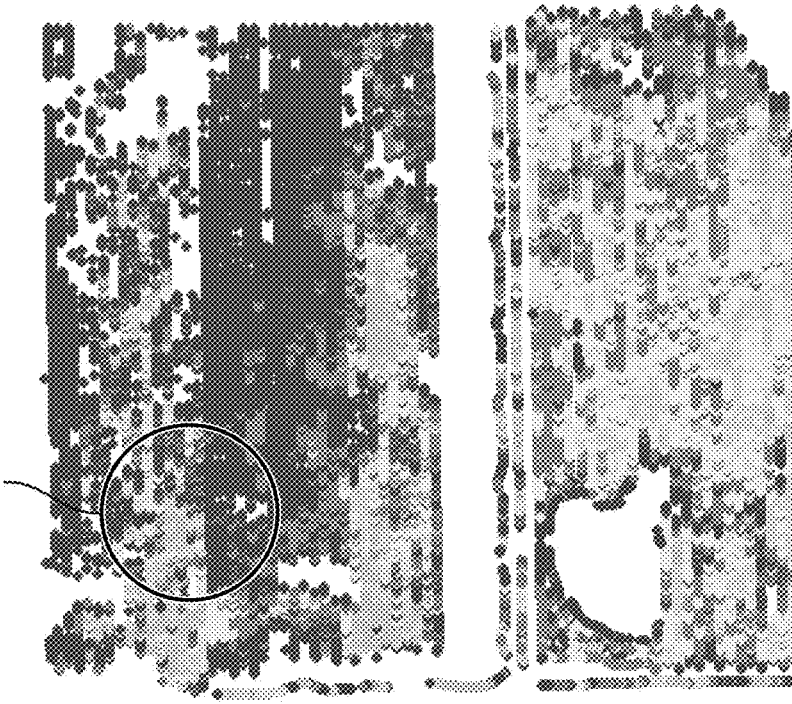
FIG. 11A illustrates uncalibrated yield data points of FIG. 10, according to one embodiment.

One assumption made in the initial calibration, outlier, and data partitioning methods is that all machines will generally share similar yield data distributions. This assumption relies on its own assumption: that each machine covers areas of similar yield. In the example illustrated in the data partitioning section, this assumption is valid: both machines have field-wide coverage, and thus have exposure to all of the different production zones. However, the machine coverage map illustrated in FIG. 10 illustrates an example situation where this assumption does not hold. As illustrated in FIG. 10, two machines cover very different areas of a field 1000. 1010A, 1020A, and 1030A illustrate coverage of a first machine and 1010B, and 1020B illustrate coverage of a second machine. Hence, a common distribution between the two machines is expected if the field has relatively uniform yield throughout. However, this is not always the case, particularly for large fields, and contradicts the assumption of field variability that underlies zone management. FIG. 11A illustrates uncalibrated yield data points for the field 1000 in FIG. 10, confirming the idea of yield variability: the south half of the field 1000 (including 1030A and some of 1020B) produced stronger yields than the north half of the field 1000 (including 1010A, 1010B, 1020A, and some of 1020B). In summary, it is expected that fields will vary spatially, and in cases where machines cover different regions, the current calibration techniques may not be appropriate.

To see why the initial calibration, outlier, and data partitioning methods are insufficient for such cases, consider again the uncalibrated yield data points for the field 1000 in FIG. 10 illustrated in FIG. 11A. Beyond the differences in area productivity, there is a calibration issue, as the machine coverage map boundaries (illustrated in FIG. 10) are visible in the uncalibrated yield data in the north half of the field 1000 as illustrated in FIG. 11A. The uncalibrated yield data illustrated in FIG. 11A suggests that the first machine (covering 1010B and 1020B as illustrated in FIG. 10) is measuring higher yield data point values than the second machine (covering 1010A, 1020A, and 1030A as illustrated in FIG. 10) over the same area (the north half of the field 1000). The yield data points from the first machine should be adjusted down, or the yield data points from the second machine should be adjusted up. FIG. 11B shows the results of running calibration according to the described methods (e.g., initial calibration, outlier, or data partitioning) on the uncalibrated yield points illustrated in FIG. 11A. Close inspection of FIG. 11B shows an interesting and undesirable result: the strong yields in the south half of the field 1000 illustrated in FIG. 10 covered by the second machine push up its overall field average to be higher than the first machine, and thus its yield data point values are reduced after calibration, while the first machine's are increased. In other words, the opposite of the desired result is observed, and the machine coverage boundaries become even more pronounced. This example underscores the effects of spatial variation, and the calibration methods need to be extended to handle these situations.

The data partitioning method demonstrated that certain variables (e.g. moisture content) can be controlled by running multiple calibrations and holding these variables constant for each calibration. The variable of interest in FIGS. 10 and 11A-B is location, which can be held constant over multiple calibrations. Stated another way, instead of performing a field-wide calibration, multiple localized calibrations can be performed.

There are a number of potential strategies for choosing localized zones to calibrate over. Management zones are one choice, and in one embodiment, partitioning is implemented using management zones using the functionality from the data partitioning method, provided that each yield data point is associated with a zone identifier. However, zone information is not always available. Furthermore, within-zone variability has been observed in a number of fields, particularly for zones whose polygons are distributed across large areas. Hence, a more robust solution for calibration that does not depend on management zones for localized calibration is also provided.

Variability that occurs between polygons with the same zone identifier could be mitigated by calibrating over each polygon independently. However, there are no stipulations as to the minimum size of a management zone polygon, and the calibration methods described herein are dependent on sample size which tend to be more sensitive to bias and outliers. Thus, small management zone polygons may not be the most appropriate choice for localized calibration.

Figure 12B:
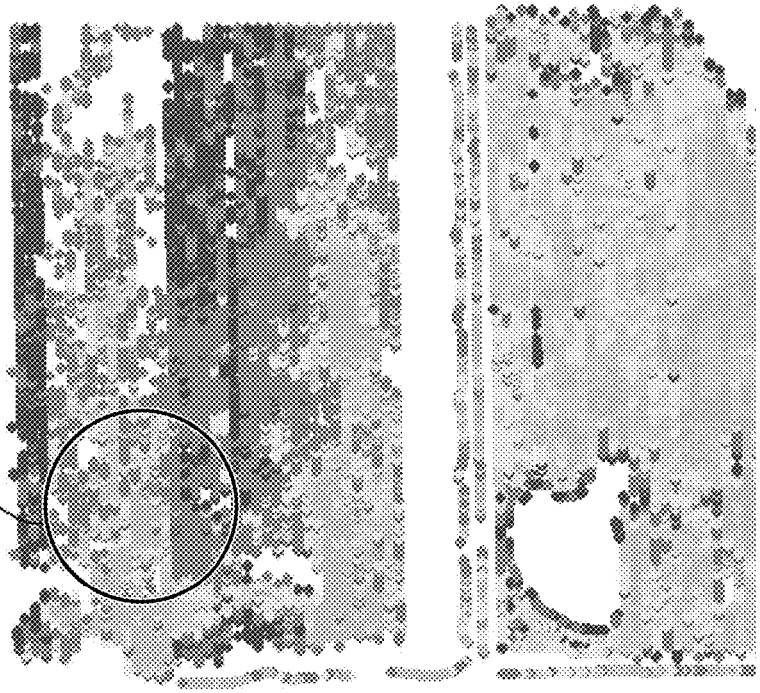
FIG. 12B illustrates calibrated yield data points of FIG. 12A calibrated according to a grid-based calibration, according to one embodiment.
Figure 12A:
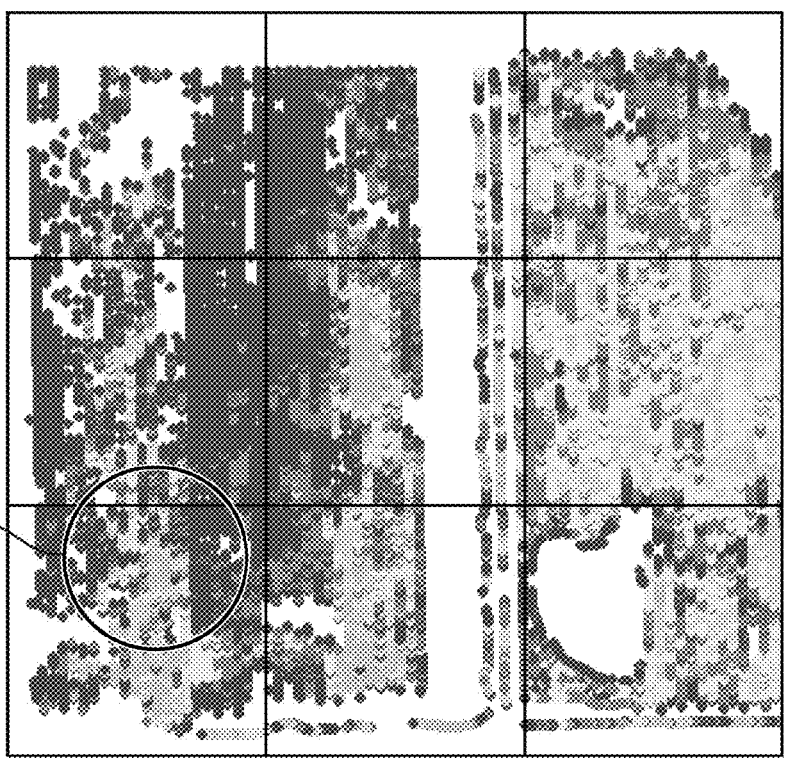
FIG. 12A illustrates a grid overlaid on uncalibrated yield data points of FIG. 11A, according to one embodiment.

One method includes overlaying a grid on a field, and calibrating each cell in the grid independently. FIG. 12A illustrates the uncalibrated yield data points of FIG. 11A with a grid overlain. FIG. 11B illustrates de-localized calibration, while FIG. 12B illustrates the result of calibrating each grid cell in FIG. 12A independently. The machine coverage boundaries that are visible in FIG. 11B are much less pronounced in FIG. 12B. As shown in FIG. 12B, the first machine's yields are driven lower in the north half of the field 1000 (a reduction in light gray on the top and bottom), while the second machine's yields are increased (an increase from dark gray to lighter gray in the middle of the north half). Hence, the localized calibration is a viable option for mitigating the effects of field variability with respect to the previously described methods (initial calibration, outlier, and data partitioning).

A method for grid-based calibration is outlined as follows:

1) Receive, by the receiver 202, groups of yield data points on a per field basis, each group associated with one or more attributes, such as, for example, a machine identifier and a localized zone identifier;

2) Divide, by the calculation module 210, the yield data points into localized zones based on the localized zone identifiers;

3) Perform the methods of initial calibration and/or outlier on the yield data points in a per localized zone basis.

VI. Neighborhood-Based Calibration

The grid-based calibration method for calibration mitigates negative effects of field-wide variability. However, the method introduces its own spatial artifact. Consider FIG. 12A with a particular region highlighted (black circle) as indicated by circle 1201. FIG. 11B illustrates yield data points calibrated using one or more of initial calibration, outlier, and data partitioning methods, and FIG. 12B illustrates yield data points calibrated using the grid-based calibration method. FIG. 12B illustrates a dark gray region near the center of circle 1203 that is more pronounced than its neighbors. One reason this can occur is because of the grid cell that the data yield data points are located in: the other yield data points for that particular machine are strong in that grid cell, and subsequently, those yield data points get reduced. Because that region highlighted by the circle 1201 illustrated in FIG. 12A has weak yields, the result is that the grid cell is adjusted to be even weaker as illustrated in FIG. 12B. However, the correctness of this calibration is questionable, given that this small region highlighted by the circle 1203 as illustrated in FIG. 12B is attached to a much larger region that has similar low production rates (grid cell to the right as illustrated in FIG. 12A). However, because of the dividing lines of the grid cell, these nearby points are not considered in the calibration of the particular grid cell.

A potential mitigation for this effect is to reduce the size of the grid cells to minimize the distance between grid cell center and grid cell edge. This solution is straightforward, but lacks robustness, for two reasons:

1) Larger grid cell sizes have advantages under the described methods (e.g., initial calibration, outlier, and data partitioning), and this may bound the minimum grid cell size that can be considered, particularly if the yield data points are sparse (e.g. higher machine velocities).

2) Calibration occurs by resolving discrepancies between the yield data point values of multiple machines. Thus, coverage in grid cells by at least two machines produces desirable results. Reducing the size of grid cells reduces the probability of overlap by multiple machines; in the extreme case, the grid cell size could be reduced so that no overlap occurs (and thus the described methods (e.g., initial calibration, outlier, and data partitioning) have no effect).

Under the assumption that the calibration value for a particular yield data point should be based upon the yield data point values of its closest neighbors, a possible method of calibration is to perform a per-point calibration.

A method for neighborhood-based calibration is outlined as follows:

1) Receive, by the receiver 202, groups of yield data points on a per field basis, each group associated with an attribute, such as, for example, a machine identifier;

2) For each yield data point (P)

a) Determine, by the neighborhood module 220, a set of yield data points including yield data points representing the yield data point P's neighborhood (N). For example, the yield data point P's neighborhood N can include all points within a threshold distance of the yield data point P;

b) Calibrate, by the neighborhood module 220, the yield data point P using the set of yield data points {P}+N producing a neighbor-calibrated yield data point;

4) Perform the methods of initial calibration and/or outlier using the neighbor-calibrated data points.

In other words, each yield data point becomes the center of its own calibration.

Figure 13:
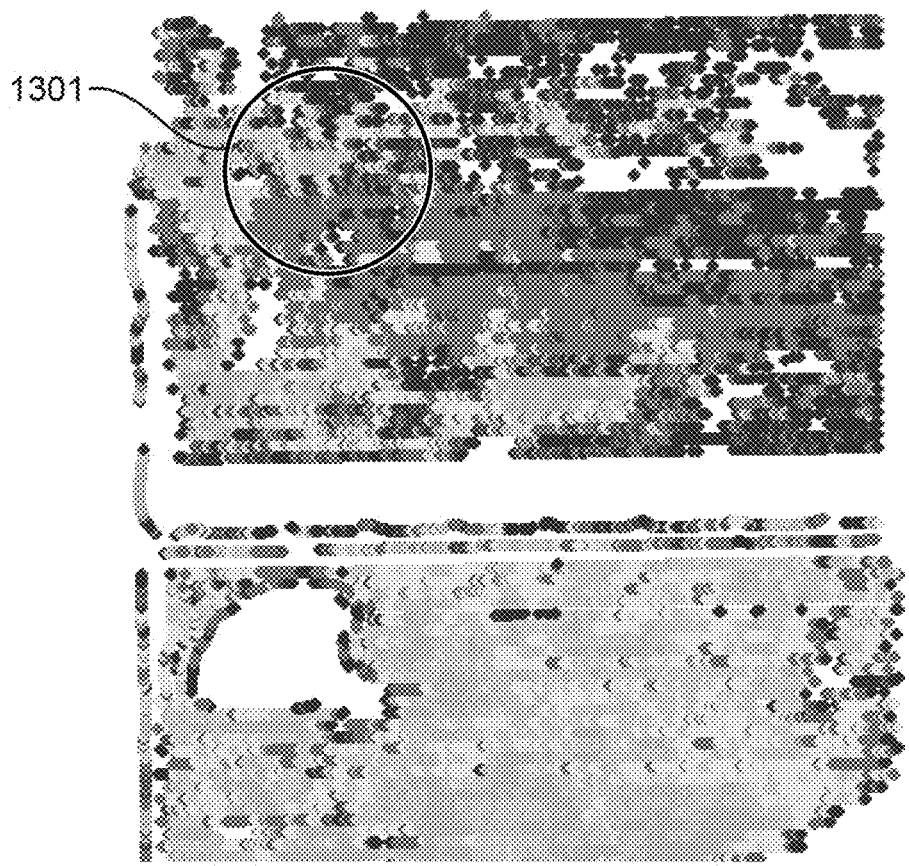
FIG. 13 illustrates calibrated yield data points of FIG. 11A according to a neighborhood-based calibration, according to one embodiment.

FIG. 11B illustrates calibrated yield data points according to initial calibration, outlier, and/or data partitioning methods, FIG. 12B illustrates calibrated yield data points according to the grid-based calibration method and FIG. 13 illustrates calibrated yield data points according to neighborhood-based calibration with a threshold distance of 30 meters. The neighborhood-based calibration illustrated in FIG. 13 shows similar results as the grid-based calibration illustrated in FIG. 12B; however, the neighborhood-based calibration reduces the local artifacts introduced in the grid-based calibration and is illustrated by comparing the particular region highlighted (black circle) as indicated by 1203 in FIG. 12B and the particular region highlighted (black circle) as indicated by 1301 in FIG. 13.

While the advantages of neighborhood-based calibration are apparent, there is one primary disadvantage that maintains the relevancy of the grid-based calibration method: the computational costs of the neighborhood-based calibration are considerably higher than those of the grid-based calibration. The number of calibrations that occur in the grid-based methods are G, where G is the number of grid cells, while the number of calibrations that occur in the neighborhood-based methods are M, where M is the number of yield data points. For reasonable grid cell sizes, G will be orders of magnitude smaller than M. Furthermore, determining the neighboring yield data points of a single yield data point is computationally expensive as well, modeled using a linear-time operation in the worst case. Algorithmically speaking, neighborhood-based calibration methods increase the running time of calibration from linear to quadratic, which means that the ratios between the running times of the two calibration methods, the neighborhood-based calibration and the grid-based calibration, will increase as the number of data points grows. Hence, while the neighborhood-based calibration provides the most justifiable calibration, the grid-based calibration may represent a reasonable approximation in situations where dissemination of results is time-critical.

VII. Confidence Calibration

The described methods (e.g., initial calibration, outlier, data partitioning, grid-based calibration and neighborhood-based calibration) apply an adjustment to each machine in the dataset. Within a calibration zone, machines with higher observed yields will be reduced, while machines with lower observed yields will be increased. In one embodiment, a calibration is a resolution of between-machine variation. Calibration relates to resolving discrepancies in measurements with a known standard. Adjusting yield data points to match volume measured by weight would be a more appropriate example of calibration.

In one example, a subset of the machines that have been calibrated is known. For example, suppose there are two machines, a first machine and a second machine, with the first machine observing higher yields than the second machine. If there is a higher confidence that the first machine is accurate (e.g. due to previous calibration, or more accurate machine/implement), then the second machine's observed values can be adjusted to match the first machine's, rather than adjusting each result equally to some average of the two. For example, the first machine's observed values can be weighted higher (e.g., multiplied by a factor of 2) and the second machine's observed values can be weighted lower (e.g., multiplied by a factor of ½).

Figure 14B:
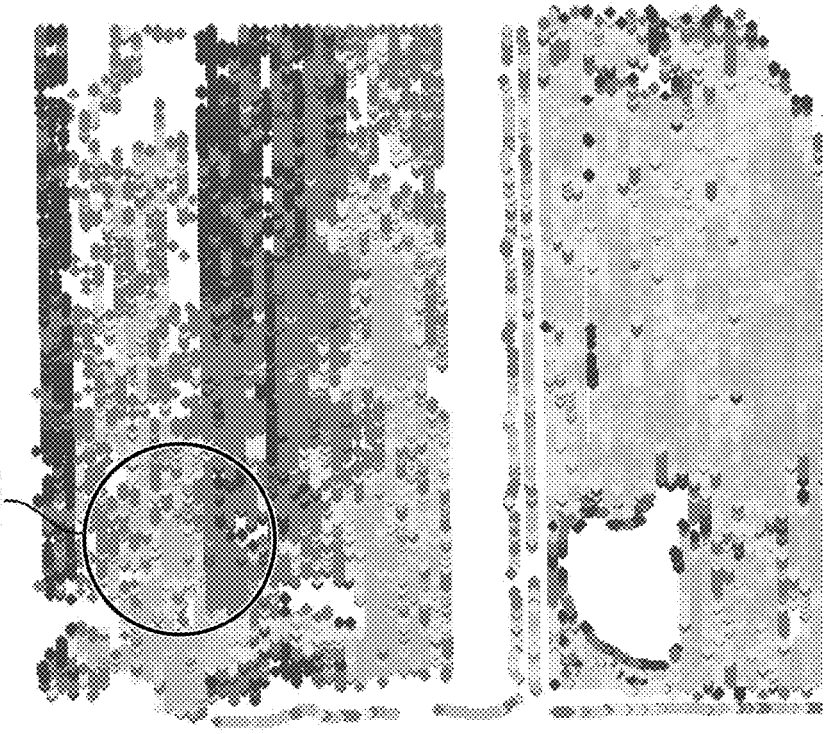
FIG. 14B illustrates calibrated yield data points of FIG. 11A with full confidence in a second machine, according to one embodiment.
Figure 14A:
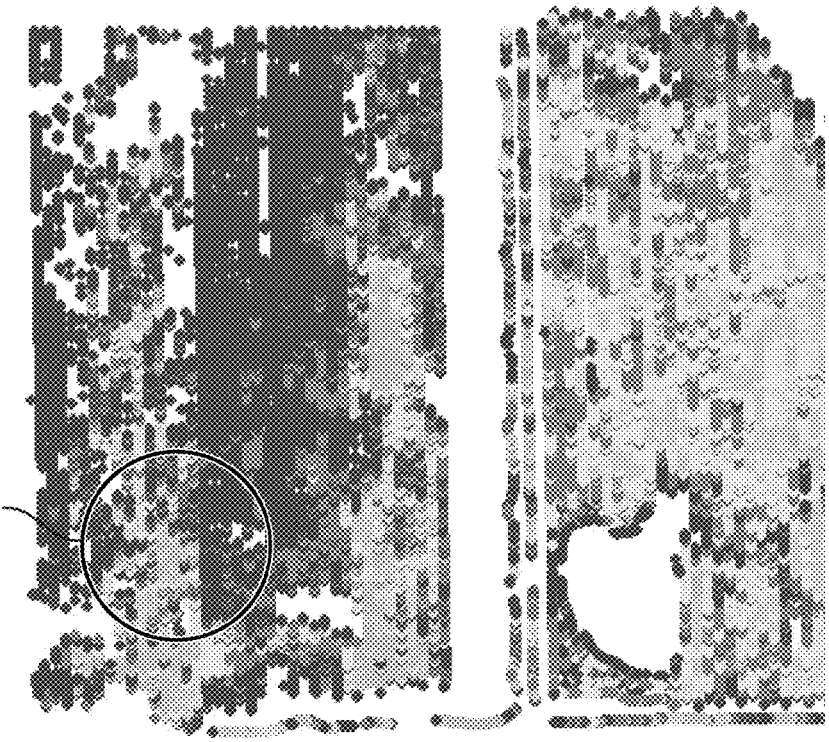
FIG. 14A illustrates calibrated yield data points of FIG. 11A with full confidence in a first machine, according to one embodiment.

To allow for per-machine calibration, confidences can be associated with each machine in the calibration set. Yield data points associated with high-confidence machines will be used to calibrate yield data points associated with low confidence machines. This extension can have considerable effects on the results of calibration. FIGS. 14A-14B illustrate the field-wide calibration using (a) full confidence in the first machine as illustrated in FIG. 14A, and (b) full confidence in the second machine as illustrated in FIG. 14B.

The confidence mechanism is not limited to simply designating one machine as the calibration standard. For example, suppose there are four machines: a first machine, a second machine, a third machine and a fourth machine. If it is known that both the first and second machines have been calibrated, but the third and fourth machines has not, full confidence can be assigned to both the first and second machines, and subsequently, the third and fourth machine' yield data values will be calibrated based on the averages of the first and second machines. In theory, if both the first and second machines are calibrated, then the two machines are expected to produce identical yield data point distributions in the same localized zone. In practice, even calibrated machines can suffer errors in their observations (e.g., outliers). Under the assumption that these errors are independent and rare, the first and second calibrated machines should have low co-occurrences of errors, and thus the errors occurring in the first machine will be offset by the lack of errors in the second machine for each calibration zone (and vice versa) particularly when medians are used (as described in the outlier method) as opposed to means (as described in the initial calibration method). The more "known" data, the higher the stability of the calibration standard.

In another embodiment, the confidence values can be generalized from a binary system (low-confidence/high confidence) to a continuous value between 0 (i.e., no confidence) and 1 (i.e., absolutely confident). This allows a spectrum of confidences. The generalized binary system and/or the continuous value system can be implemented by calibrating yield data points, for example, by weighting the yield data points based on the confidence values. Statements such as "the user is twice as confident in the first machine as he/she is in the second machine" can be applied to calibrate the machines appropriately. The statement can be applied by calibrating the yield data points of the first and second machines. For example, the statement can be applied by weighting each yield data point of the second machine by the confidence value of the second machine (e.g., ½) and weighting each yield data point of the first machine by the confidence value of the first machine (e.g., 1). This method can be used to produce a compromise between full-confidence and no confidence.

A method for confidence calibration is outlined as follows:

1) Receive, by the receiver 202, groups of yield data points on a per field basis, each group associated with one or more attributes and each attribute associated with a confidence parameter;

2) Calibrate, by the confidence module 230, yield data points of each group based on the confidence parameter associated with the attribute of the group producing confidence-calibrated yield data points;

3) Perform the methods of initial calibration and/or outlier using the confidence-calibrated yield data points.

VIII. Post-Calibration Processing

One of the underlying assumptions of calibration is that there is multiple machine coverage in each calibration zone. Localized calibration methods, combined with regional machine coverage examples as illustrated in FIG. 10, mean that it is likely that many cases will occur where no calibration occurs in particular zones. Accepting calibration in this manner makes a strange assumption: that calibration of a machine should only occur in certain zones. Calibration issues show temporal dependence (i.e. calibration degrades over harvest), but the assumptions of a similar spatial dependence seems less intuitive.

For example, consider two machines (a first machine and a second machine), and suppose that in the calibration zones, the calibration method applies a reasonably consistent adjustment to each yield data point of the first machine (for example, an increase of 4 bu/ac in almost all cases). In such a case, it might be reasonable to assume that the machine and/or implement is "low" by 4 bu/ac, and subsequently, every yield data point measured by the first machine should be increased by this amount. On the other hand, if the amount of calibration is varied (e.g. from −4 bu/ac to 19 bu/ac), then applying a constant adjustment across the field for each of the yield data points would likely not be appropriate.

Hence, consider the application of a field-wide adjustment of all yield data points for a particular machine subsequent to the calibration operation. This adjustment occurs only under circumstances where the calibrations of a particular machine are consistent. For the adjustment, consider two potential adjustments:

a) Bias: a number X that will be added to each yield data point measured by a particular machine;

b) Ratio: a percentage X that will be added to each yield data point measured by a particular machine.

Both the bias and the ratio are calculated as the mean or median of the calibrations that occur in all calibration zones relative to a particular machine. For example, if the average or median adjustment to the first machine's data was 4 bu/ac in the calibration zones, then a bias amount of 4 bu/ac would be added to the first machine's yield data points field-wide as a corrective measure. When using ratios, if a consistent percentage is added to the first machine's data in the calibration zones (e.g. 8%), then this percentage would be added to all yield data points of the first machine. In the case of using the bias adjustment, the within machine variation for each machine is maintained, as a constant value is being applied to each of its yield data points. The calibrations adjust yield data point values relative to other machines, not to yield data point values measured by the same machine.

For determining when such field-wide adjustment is appropriate, the standard deviation of the adjustments is measured within the calibration zones. If the standard deviation falls below a predetermined threshold, the numbers are considered to be consistent, and global calibration will occur.

A method for post-calibration processing is outlined as follows:

1) Access, by the post calibration module 240, a predetermined adjustment value for each group of a plurality of groups, where the predetermined adjustment value for a group is associated with an attribute of the group;

2) Adjust, by the post calibration module 240, each calibrated yield data point of a group based on the predetermined adjustment value for the group.

IX. Calibrating Yield Data Points

Figure 15:
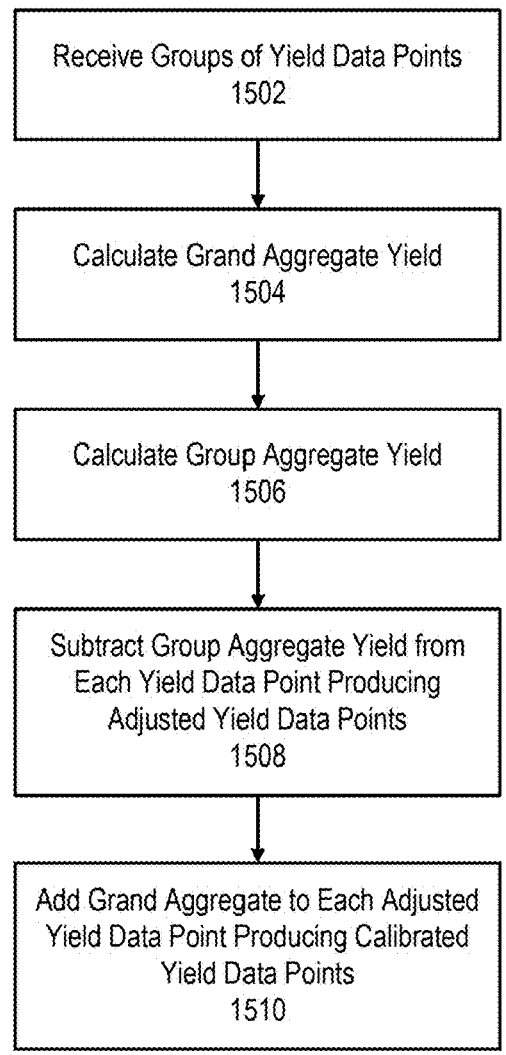
FIG. 15 is a flowchart of an example process for calibrating yield data points, according to one embodiment.

FIG. 15 illustrates a flow chart of a method of calibrating yield data points, according to one embodiment. The receiver 202 receives 1502 a plurality of groups of yield data points, where each group is associated with an attribute. The attribute that each group is associated with includes at least one of: a machine identifier, a zone identifier, a localized zone identifier, a moisture identifier, and any combination thereof. The grand aggregate calculation module 212 calculates 1504 a grand aggregate yield based on yield data points of the plurality of groups. For each group of the plurality of groups, the group aggregate calculation module 214 calculates 1506 a group aggregate yield based on the yield data points of the group. The calculation module 210 subtracts 1508 the group aggregate yield from each yield data point in the group producing adjusted yield data points. The calculation module 210 adds 1510 the grand aggregate yield to each of the adjusted yield data points producing calibrated yield data points.

X. Computing Machine Architecture

Figure 16:
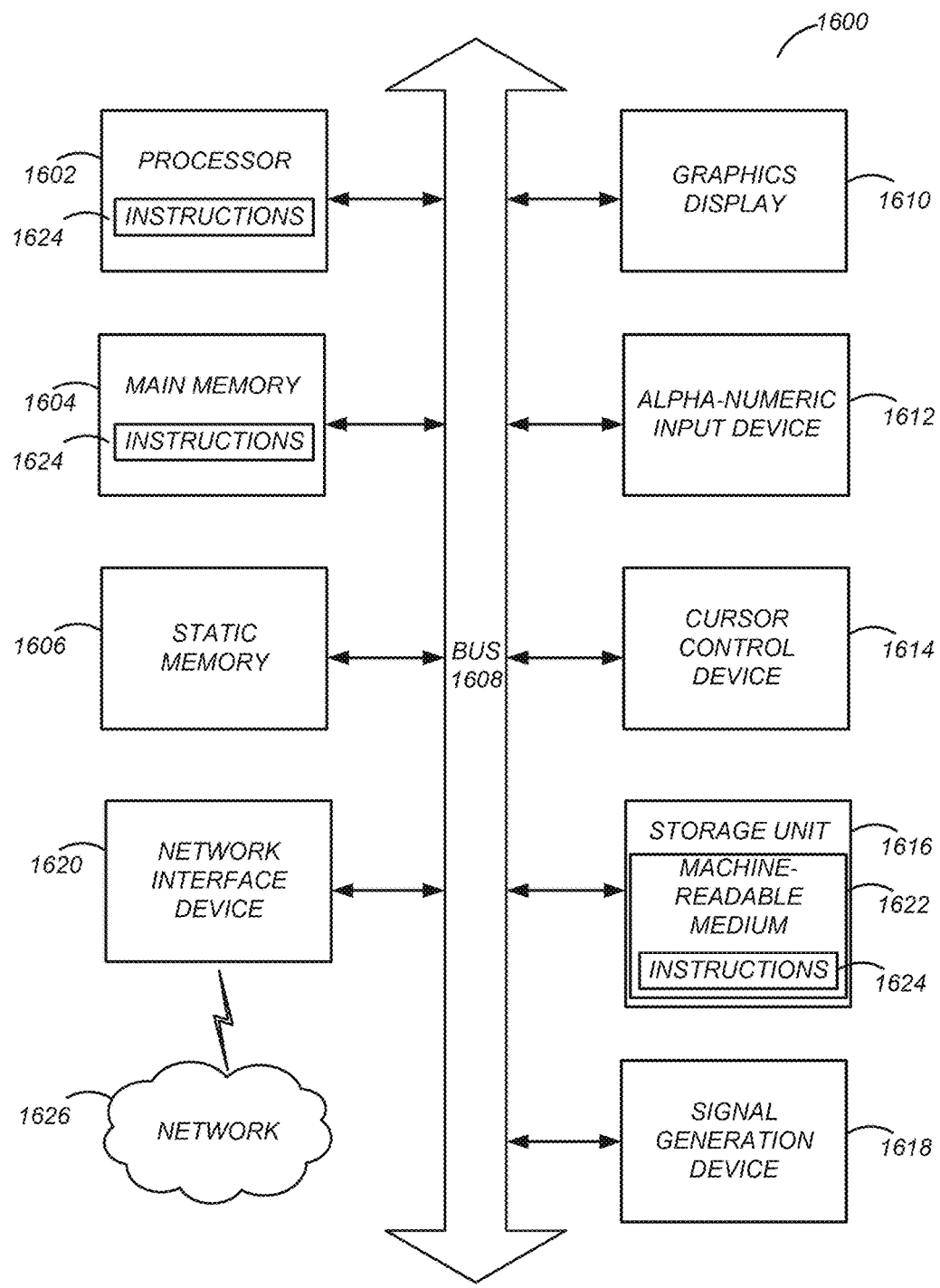
FIG. 16 illustrates one embodiment of components of an example machine able to read instruction from a machine-readable medium and execute them in a processor (or controller).

FIG. 16 is a block diagram illustrating components of an example machine able to read instructions from a machine-readable medium and execute them in a processor (or controller). Specifically, FIG. 16 shows a diagrammatic representation of a machine in the example form of a computer system 1600 within which instructions 1624 (e.g., program code or software) for causing the machine to perform any one or more of the methodologies discussed herein may be executed. In alternative embodiments, the machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The machine may be a server computer, a client computer, a personal computer (PC), a tablet PC, a set-top box (STB), a personal digital assistant (PDA), a cellular telephone, a smartphone, a web appliance, a network router, switch or bridge, or any machine capable of executing instructions 1624 (sequential or otherwise) that specify actions to be taken by that machine. Further, while only a single machine is illustrated, the term "machine" shall also be taken to include any collection of machines that individually or jointly execute instructions 1624 to perform any one or more of the methodologies discussed herein.

The example computer system 1600 includes a processor 1602 (e.g., a central processing unit (CPU), a graphics processing unit (GPU), a digital signal processor (DSP), one or more application specific integrated circuits (ASICs), one or more radio-frequency integrated circuits (RFICs), or any combination of these), a main memory 1604, and a static memory 1406, which are configured to communicate with each other via a bus 1608. The computer system 1600 may further include graphics display unit 1610 (e.g., a plasma display panel (PDP), an organic light emitting diode (OLED) display, a liquid crystal display (LCD), a projector, or a cathode ray tube (CRT)) and corresponding display drivers. The computer system 1600 may also include alphanumeric input device 1612 (e.g., a keyboard), a cursor control device 1614 (e.g., a mouse, a trackball, a joystick, a motion sensor, or other pointing instrument), a storage unit 1616, a signal generation device 1618 (e.g., a speaker), and a network interface device 1620, which also are configured to communicate via the bus 1608.

The storage unit 1616 includes a machine-readable medium 1622 on which is stored instructions 1624 (e.g., software) embodying any one or more of the methodologies or functions described herein. The instructions 1624 (e.g., software) may also reside, completely or at least partially, within the main memory 1604 or within the processor 1602 (e.g., within a processor's cache memory) during execution thereof by the computer system 1600, the main memory 1604 and the processor 1602 also constituting machine-readable media. The instructions 1624 (e.g., software) may be transmitted or received over a network 1626 via the network interface device 1620.

While machine-readable medium 1622 is shown in an example embodiment to be a single medium, the term "machine-readable medium" should be taken to include a single medium or multiple media (e.g., a centralized or distributed database, or associated caches and servers) able to store instructions (e.g., instructions 1624). The term "machine-readable medium" shall also be taken to include any medium that is capable of storing instructions (e.g., instructions 1624) for execution by the machine and that cause the machine to perform any one or more of the methodologies described herein. The term "machine-readable medium" includes, but not be limited to, data repositories in the form of solid-state memories, optical media, and magnetic media.

XI. Additional Configuration Considerations

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms. Modules may constitute either software modules (e.g., code embodied on a machine-readable medium or in a transmission signal) or hardware modules. A hardware module is a tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

The various operations of example methods described herein may be performed, at least partially, by one or more processors, e.g., processor 1602, that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs)).

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for post-harvest yield data calibration through the principles described herein. Thus, while particular embodiments and applications have been illustrated and described, it is to be understood that the described embodiments are not limited to the precise construction and components described herein. Various modifications, changes and variations, which will be apparent to those skilled in the art, may be made in the arrangement, operation and details of the method described herein.

The invention claimed is:

1. A method comprising:
    receiving, from multiple harvesting machines, a plurality of groups of yield data points recorded by uncalibrated sensors mounted to each machine of the multiple harvesting machines as the multiple harvesting machines harvest plants in a field, the yield data points representing uncalibrated data recorded by the multiple harvesting machines and corresponding to a yield harvested from the plants by each respective machine of the multiple harvesting machines;
    associating each group of yield data points with a machine identifier indicating the machine of the multiple harvesting machines used to record the group of yield data points;
    calculating a grand aggregate yield for the field based on yield data points of the plurality of groups received from the plurality of machines;
    for each group of the plurality of groups:
        calculating a group aggregate yield based on yield data points of the group associated with each machine identifier;
        subtracting the group aggregate yield from each yield data point of the group producing adjusted yield data points;
        producing calibrated yield data points for each of the harvesting machines by adding the grand aggregate yield to each of the adjusted yield data points; and
    storing, in computer memory, the calibrated yield data points in place of returning the initially received yield data points.

2. The method of claim 1, wherein the grand aggregate yield is a grand mean yield and the group aggregate yield is a group mean yield.

3. The method of claim 1, wherein the grand aggregate yield is a grand median yield and the group aggregate yield is a group median yield.

4. The method of claim 1, further comprising:
    for each yield data point:
    determining a set of yield data points including yield data points within a threshold distance of the yield data point; and
    calibrating the yield data point based on the set of yield data points producing a neighbor-calibrated yield data point.

5. The method of claim 1, further comprising:
    for each group of the plurality of groups:
    receiving a confidence parameter associated with the attribute; and
    calibrating yield data points of the group based on the confidence parameter producing confidence-calibrated yield data points.

6. The method of claim 1, further comprising:
    for each group of the plurality of groups:
    accessing a predetermined adjustment value for the group, the predetermined adjustment value associated with the attribute; and
    adjusting each of the calibrated yield data points by the predetermined adjustment value.

7. A system comprising:
    a non-transitory computer-readable storage medium storing executable computer instructions that, when executed, perform steps comprising:
        receiving, from multiple harvesting machines, a plurality of groups of yield data points recorded by uncalibrated sensors mounted to each machine of the multiple harvesting machines as the multiple harvesting machines harvest plants in a field, the yield data points representing uncalibrated data recorded by the multiple harvesting machines and corresponding to a yield harvested from the plants by each respective machine of the multiple harvesting machines;
        associating, each group of yield data points with a machine identifier indicating the machine of the multiple harvesting machines used to record the group of yield data points;

calculating a grand aggregate yield for the field based on yield data points of the plurality of groups received from the plurality of machines;

for each group of the plurality of groups:

calculating a group aggregate yield based on yield data points of the group associated with each machine identifier;

subtracting the group aggregate yield from each yield data point of the group producing adjusted yield data points;

producing calibrated yield data points for each of the harvesting machines by adding the grand aggregate yield to each of the adjusted yield data points; and storing, in computer memory, the calibrated yield data points in place of returning the initially received yield data points;

a processor configured to execute the computer instructions.

8. The system of claim 7, wherein the grand aggregate yield is a grand mean yield and the group aggregate yield is a group mean yield.

9. The system of claim 7, wherein the grand aggregate yield is a grand median yield and the group aggregate yield is a group median yield.

10. The system of claim 7, wherein the instructions, when executed, perform further steps comprising:

for each yield data point:

determining a set of yield data points including yield data points within a threshold distance of the yield data point; and calibrating the yield data point based on the set of yield data points producing a neighbor-calibrated yield data point.

11. The system of claim 7, wherein the instructions, when executed, perform further steps comprising:

for each group of the plurality of groups:

receiving a confidence parameter associated with the attribute; and calibrating yield data points of the group based on the confidence parameter producing confidence-calibrated yield data points.

12. The system of claim 7, wherein the instructions, when executed, perform further steps comprising:

for each group of the plurality of groups:

accessing a predetermined adjustment value for the group, the predetermined adjustment value associated with the attribute; and adjusting each of the calibrated yield data points by the predetermined adjustment value.

13. A non-transitory computer-readable storage medium storing executable computer instructions that, when executed by a processor, perform steps comprising:

receiving, from multiple harvesting machines, a plurality of groups of yield data points recorded by uncalibrated sensors mounted to each machine of the multiple harvesting machines as the multiple harvesting machines harvest plants in a field, the yield data points representing uncalibrated data recorded by the multiple harvesting machines and corresponding to a yield harvested from the plants by each respective machine of the multiple harvesting machines;

associating, each group of yield data points with a machine identifier indicating the machine of the multiple harvesting machines used to record the group of yield data points;

calculating a grand aggregate yield for the field based on yield data points of the plurality of groups received from the plurality of machines;

for each group of the plurality of groups:

calculating a group aggregate yield based on yield data points of the group associated with each machine identifier;

subtracting the group aggregate yield from each yield data point of the group producing adjusted yield data points;

producing calibrated yield data points for each of the harvesting machines by adding the grand aggregate yield to each of the adjusted yield data points; and storing, in computer memory, the calibrated yield data points in place of returning the initially received yield data points.

14. The non-transitory computer-readable storage medium of claim 13, wherein the grand aggregate yield is a grand mean yield and the group aggregate yield is a group mean yield.

15. The non-transitory computer-readable storage medium of claim 13, wherein the grand aggregate yield is a grand median yield and the group aggregate yield is a group median yield.

16. The non-transitory computer-readable storage medium of claim 13, wherein the instructions, when executed by the processor, perform further steps comprising:

for each yield data point:

determining a set of yield data points including yield data points within a threshold distance of the yield data point; and calibrating the yield data point based on the set of yield data points producing a neighbor-calibrated yield data point.

17. The non-transitory computer-readable storage medium of claim 13, wherein the instructions, when executed by the processor, perform further steps comprising:

for each group of the plurality of groups:

receiving a confidence parameter associated with the attribute; and calibrating yield data points of the group based on the confidence parameter producing confidence-calibrated yield data points.

18. The non-transitory computer-readable storage medium of claim 13, wherein the instructions, when executed by the processor, perform further steps comprising:

for each group of the plurality of groups:

accessing a predetermined adjustment value for the group, the predetermined adjustment value associated with the attribute; and adjusting each of the calibrated yield data points by the predetermined adjustment value.

19. The method of claim 1, wherein the grand aggregate yield for the field is determined over a defined period of time during which the harvesting machines harvested plants in a field.

20. The system of claim 7, wherein the grand aggregate yield for the field is determined over a defined period of time during which the harvesting machines harvested plants in a field.

21. The non-transitory computer-readable storage medium of claim 13, wherein the grand aggregate yield for the field is determined over a defined period of time during which the harvesting machines harvested plants in a field.

* * * * *